(12) United States Patent
Crisalle et al.

(10) Patent No.: US 10,211,470 B2
(45) Date of Patent: Feb. 19, 2019

(54) OPERATIONAL CONTROL OF FUEL CELLS

(71) Applicant: University of Florida Research Foundation, Inc., Gainesville, FL (US)

(72) Inventors: Oscar D. Crisalle, Gainesville, FL (US); Mohammad A. R. Biswas, Gainesville, FL (US); Shyam Prasad Mudiraj, Gainesville, FL (US); William E. Lear, Jr., Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 642 days.

(21) Appl. No.: 14/771,583

(22) PCT Filed: Mar. 11, 2014

(86) PCT No.: PCT/US2014/023117
§ 371 (c)(1),
(2) Date: Aug. 31, 2015

(87) PCT Pub. No.: WO2014/164650
PCT Pub. Date: Oct. 9, 2014

(65) Prior Publication Data
US 2016/0020476 A1    Jan. 21, 2016

Related U.S. Application Data

(60) Provisional application No. 61/776,464, filed on Mar. 11, 2013.

(51) Int. Cl.
*H01M 8/04186* (2016.01)
*H01M 8/1011* (2016.01)
(Continued)

(52) U.S. Cl.
CPC ....... *H01M 8/04186* (2013.01); *A61K 31/202* (2013.01); *H01M 8/04067* (2013.01);
(Continued)

(58) Field of Classification Search
None
See application file for complete search history.

(56) References Cited

U.S. PATENT DOCUMENTS 6,589,679 B1    7/2003  Acker et al.
6,762,587 B1    7/2004  Barbetta
(Continued)

FOREIGN PATENT DOCUMENTS

JP    2006114487 A    4/2006

OTHER PUBLICATIONS

International Search Report for PCT/US2014/023117 dated Jul. 10, 2014.
(Continued)

*Primary Examiner* — Rena Dye Cronin
(74) *Attorney, Agent, or Firm* — Thomas | Horstemeyer, LLP

(57) ABSTRACT

Various examples are provided for operational control of fuel cells. In one example, among others, a system for controlling a fuel cell includes a stack temperature controller in cascade with a liquid level controller. The liquid level controller can provide a control output based at least in part upon an indication of a liquid level of a liquid fuel tank and a level reference. The stack temperature controller can provide a fan speed control output based at least in part upon an indication of a stack temperature of the fuel cell and the control output of the liquid level controller. In another example, a system for estimating methanol concentration of a fuel cell system includes a state observer that generates an estimate of the methanol concentration of fuel provided to a
(Continued)

direct methanol fuel cell based upon a plurality of states of the fuel cell system.

18 Claims, 12 Drawing Sheets

(51) Int. Cl.

| | |
|---|---|
| *H01M 8/0432* | (2016.01) |
| *H01M 8/0444* | (2016.01) |
| *H01M 8/04701* | (2016.01) |
| *H01M 8/04746* | (2016.01) |
| *H01M 8/04791* | (2016.01) |
| *H01M 8/04007* | (2016.01) |
| *A61K 31/202* | (2006.01) |
| *H01M 8/04992* | (2016.01) |

(52) U.S. Cl.
CPC ... *H01M 8/04194* (2013.01); *H01M 8/04365* (2013.01); *H01M 8/04447* (2013.01); *H01M 8/04731* (2013.01); *H01M 8/04753* (2013.01); *H01M 8/04768* (2013.01); *H01M 8/04798* (2013.01); *H01M 8/04992* (2013.01); *H01M 8/1011* (2013.01); *Y02E 60/523* (2013.01)

(56) References Cited

U.S. PATENT DOCUMENTS

| | | | |
|---|---|---|---|
| 7,776,482 B2 | 8/2010 | Akiyama et al. | |
| 7,960,067 B2 | 6/2011 | Wang et al. | |
| 2005/0042487 A1 | 2/2005 | Surampudi et al. | |
| 2005/0112419 A1* | 5/2005 | Zheng | H01M 8/0267 429/440 |
| 2005/0118470 A1 | 6/2005 | Harada et al. | |
| 2006/0063053 A1 | 3/2006 | Higashionji et al. | |
| 2006/0083966 A1* | 4/2006 | Ozeki | H01M 8/04186 429/414 |
| 2007/0082244 A1 | 4/2007 | Kuriiwa | |
| 2007/0264544 A1 | 11/2007 | Jang et al. | |
| 2007/0264548 A1* | 11/2007 | Yagi | H01M 8/04194 429/415 |
| 2008/0088273 A1* | 4/2008 | Shu | H01M 8/04007 320/101 |
| 2008/0282795 A1 | 11/2008 | Zabel et al. | |
| 2011/0223507 A1* | 9/2011 | LaVen | H01M 8/04029 429/437 |
| 2012/0178008 A1* | 7/2012 | Heo | H01M 8/0432 429/434 |

OTHER PUBLICATIONS

English translation of the Abstract for JP 2006114487 A published on Apr. 27, 2006.
"Panasonic Develops Direct Methanol Fuel Cell System With High Power Output and Durability", Dec. 25, 2009, http://news.panasonic.com/press/news/official.data/data.dir/en091225-4/en091225-4.html.
Mench, Matthew M. et al.: 'An in situ method for determination of current distribution in PEM fuel cells applied to a direct methanol fuel cell' Journal of the Electrochemical Society vol. 150, No. 1, 2003, pp. A79-A85.
Olsen Berenguer, F. A. et al.: 'Design of improved fuel cell controller for distributed generation systems' International Journal of Hydrogen Energy vol. 35, No. 11, 2010, pp. 5974-5980.
Portable DMFC system with methanol sensor-less control Source: Journal of Power Sources, vol. 167 Issue 2, May 15, 2007, pp. 442-449 Author(s): C.Y. Chen, D.H. Liu, C.L. Huang, C.L. Chang.
An innovative passive DMFC technology Source: Applied Thermal Engineering, vol. 28 Issue 13, Sep. 2008, pp. 1614 to 1622 Author(s): Amir Faghri, Zhen Guo.
Overview on the challenges and developments of micro-direct methanol fuel cells (DMFC) Source: Journal of Power Sources, vol. 163 Issue 1, Jan. 2007, pp. 743-754 Author(s): S.K. Kamarudin, W.R.W. Daud, S.L. Ho, U.A. Hasran.
Characterisation of a portable DMFC stack and a methanol-feeding concept 5 Source: Journal of Power Sources, vol. 158 Issue 1, Jul. 14, 2008, pp. 177-187 Author(s): Anders Oedegaard, Christian Hentschel.

\* cited by examiner

OPERATIONAL CONTROL OF FUEL CELLS

CROSS REFERENCE TO RELATED APPLICATIONS

This application is the 35 U.S.C. § 371 national stage application of PCT Application No. PCT/US2014/023117, filed Mar. 11, 2014, which claims priority to and the benefit of, U.S. provisional application entitled "OPERATIONAL CONTROL OF FUEL CELLS" having Ser. No. 61/776,464, filed Mar. 11, 2013, both of which are hereby incorporated by reference in their entireties.

STATEMENT REGARDING FEDERALLY SPONSORED RESEARCH OR DEVELOPMENT

This invention was made with government support under agreement no. DE-EE0000476 awarded by the Department of Energy. The Government has certain rights in the invention.

BACKGROUND

Fuel cells can be used to generate electrical power for many applications such as, e.g., automobiles, emergency power sources, etc. The fuel cell is an electrochemical device that generates electricity from an external fuel. For example, a polymer electrolyte membrane (PEM) fuel cell utilizes hydrogen while a direct methanol fuel cell (DMFC) is powered by methanol. The waste products of the reaction include heat and water.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
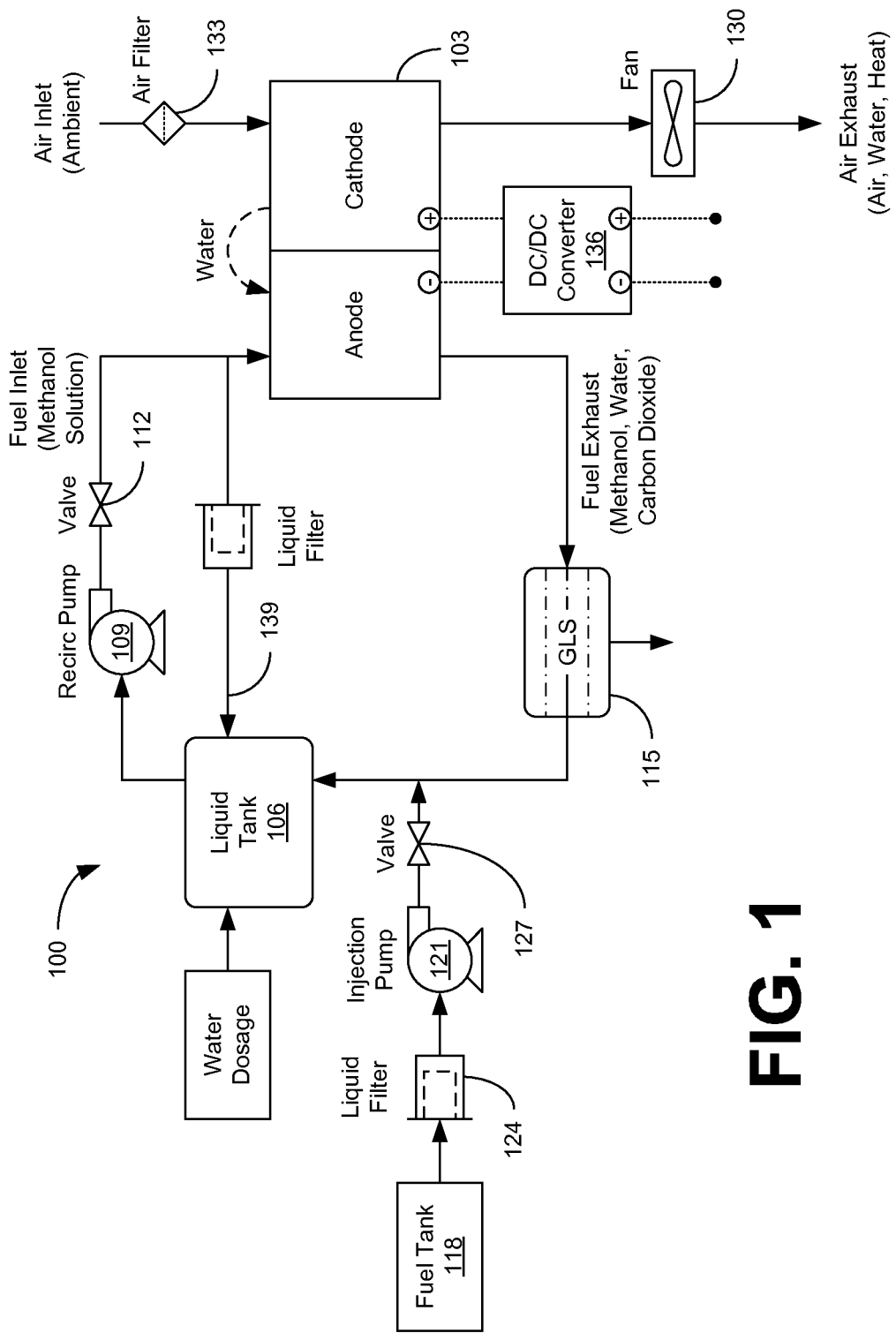
FIG. 1 is a graphical representation of a fuel cell system in accordance with various embodiments of the present disclosure.

Disclosed herein are various embodiments related to fuel cell control. Reference will now be made in detail to the description of the embodiments as illustrated in the drawings, wherein like reference numbers indicate like parts throughout the several views.

Referring to FIG. 1, shown is an example of a direct methanol fuel cell (DMFC) system 100 that may be used to provide electrical power to, e.g., electronic devices such as portable computing devices, communication devices and/or other electrically powered devices. The DMFC system 100 includes a DMFC 103 that converts a methanol solution into electrical power. Methanol is an energy dense fuel that is reasonably stable. When the methanol contacts the anode of the DMFC 103, the methanol undergoes a catalyzed oxidation reaction to produce carbon dioxide and hydrogen. Hydrogen ions that conduct across a polymer electrolyte membrane (PEM) between the anode and cathode react with oxygen to form water at the cathode. Electrons are transported through an external circuit from the anode to the cathode, providing power to connected devices. The oxidation reaction at the anode can be written as:

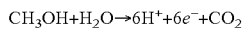

and the reduction reaction at the cathode can be written as:

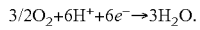

In this way, water is consumed at the anode and produced at the cathode with an overall redox reaction given by:

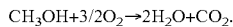

A fuel loop supplies the fuel to the DMFC 103. A liquid tank 106 contains a supply of methanol solution that is provided as fuel to the anode chamber of the DMFC 103 by a recirculation pump 109. A valve 112 may be used to adjust the amount of fuel supplied to the anode chamber of the DMFC 103. After oxidation at the anode, the fuel is exhausted as a mixture of Methanol, water, and carbon dioxide. The fuel mixture passes through a gas liquid separator (GLS) 115 to remove gas from the solution. The methanol solution is then returned to the liquid tank 106. As methanol is depleted, it can be injected into the fuel loop from a fuel tank 118 by an injection pump 121 to maintain the desired fuel concentration. A liquid filter 124 can filter the methanol before being added to the fuel loop and a valve 127 may be used to isolate the injection pump 121 from the fuel loop. A cooling fan 130 controls the airflow through the cathode chamber of the DMFC 103. Ambient air is supplied through an air filter 133 and air, water, and heat are exhausted. While a portion of the water produced at the cathode is recycled back to the anode chamber of the DMFC 103, the remaining portion is exhausted with the heated air. A water dosage may be used to add water to the liquid tank 106 to replace the water lost through the cathode.

A variety of system conditions may be monitored using sensors. These may include, but are not limited to: temperature (anode chamber, cathode chamber, and/or stack membrane) of the DMFC 103; temperature, relative humidity and/or pressure of the air supplied to and/or exiting the cathode chamber of the DMFC 103; level and temperature of the liquid tank 106; temperature of the GLS 115; methanol concentration of the fuel; stack voltage and/or stack current output by the DFMC 103, and/or the output voltage and/or current of the DC/DC converter 136.

The DMFC 103 operates in three modes or states: power production, reactivation, and water recovery. Normal modes include the power production mode where useful energy is generated by the DMFC 103 and the reactivation mode where the capabilities of the DMFC 103 are refreshed. The water recovery mode allows the liquid tank level to return to safely return to the operational range. The water recovery mode is triggered as a remedial correction to the DMFC system 100.

Water management is an important consideration for the DMFC 103. The water balance can be controlled to provide efficient operation of the DMFC 103 during the power production mode. By controlling the heating of the DMFC 103, it is possible to adjust for water loss in the exhausted air. This may be accomplished by controlling the fan speed and thus the air flow through the cathode chamber of the DMFC 103. Fuel concentration, which can affect the oxidation reaction as the anode, maybe controlled by adjusting the speed of the injection pump 121. Output current of the DMFC 103 may also be controlled via a DC/DC converter 136. The DMFC system 100 can also make real-time adjustments to respond to changes in the power load demand.

Control of the DMFC system 100 is provided by using various proportional-integral (PI) controllers that include a bias element (or PIB). The PIB control output u(t) may be expressed as:

$$u(t) = \bar{u} + K_p e(t) + K_I I(t)$$

where $\bar{u}$ is an applied bias, $K_p$ is a proportional gain, e is the error given by the difference (r−y) between a reference set point (r) and a measured (or estimated) variable (y), $K_I$ is the integral gain, and I(t) is the integral term:

$$I(t) = \int_0^t e(\tau) d\tau.$$

A positive error increases the integral term over time and a negative error decreases the integral term over time. As can be understood, this can cause the integral term to continue to increase or decrease indefinitely. This can result in unbounded control signals. Generally, an output u(t) of the PIB is limited to within an operating range defined by maximum and minimum values, which may be expressed as a saturation function: sat(u, $u_{max}$, $u_{min}$). In the case of a discrete-time implementation with a sampling period of $\Delta t$, the integral term is implemented as t=k $\Delta t$ giving:

$$I(k\Delta t) = I((k-1)\Delta t) + f(e(k\Delta t))$$

with I(0)=0. Various integral calculation schemes may be used such as, e.g., the Euler method f(e(k $\Delta t$))=e(k $\Delta t$)·$\Delta t$.

Control of the DMFC system 100 may be provided using a plurality of PIB controllers. Control of the DMFC system 100 can be implemented using processing circuitry. In various embodiments, the processing circuitry is implemented as at least a portion of a microprocessor. The processing circuitry may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. In yet other embodiments, the processing circuitry may include one or more software modules executable within one or more processing circuits. The processing circuitry may further include memory configured to store instructions and/or code that cause the processing circuitry to execute various control functions. For the exemplary DFMC system 100 of FIG. 1, four PIB controllers may be used: a stack voltage controller, a methanol concentration controller, a tank level controller, and a stack temperature controller.

Figure 2:
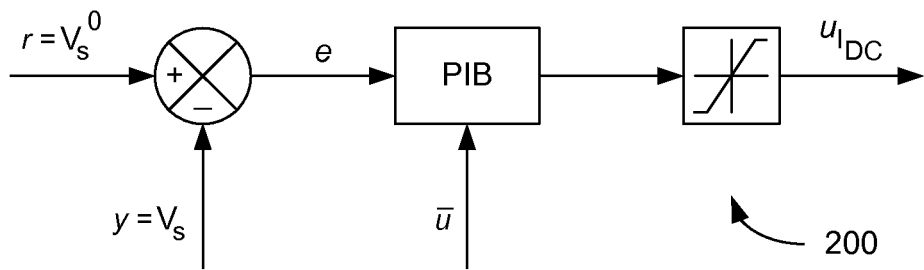
FIGS. 2-6 are graphical representations of examples of controllers for the fuel system of FIG. 1 in accordance with various embodiments of the present disclosure.
Figure 3:
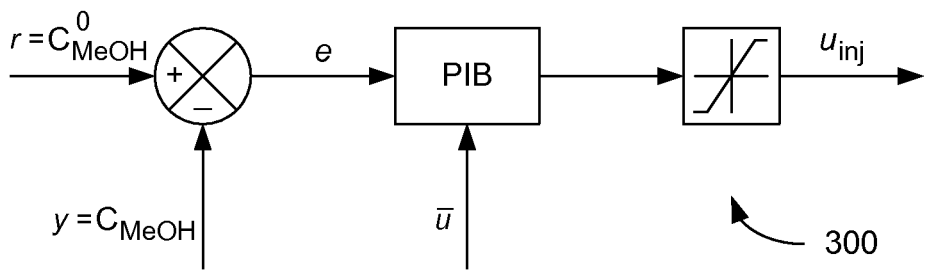

Referring to FIG. 2, shown is a graphical representation of an example of a stack voltage controller 200. An indication of the stack voltage ($V_s$) is compared to a reference setpoint ($V_s^0$) to determine an error (e), which is provided to the PIB. The PIB integrates the error and combines the scaled integral term with the scaled error and the bias term ($\bar{u}$). For example, the stack voltage may be measured between the anode and cathode of the DFMC 103. The output of the PIB is to provide the control output ($u_{I_{DC}}$) for the stack current for the DC/DC converter 136. The PIB output may be limited between, e.g., an upper limit $u_{max}$ and a lower limit $u_{min}$ of the stack current. Referring to FIG. 3, shown is a graphical representation of an example of a methanol concentration controller 300. An indication of the methanol concentration ($C_{MeOH}$) is compared to a reference setpoint ($C_{MeOH}^0$) to determine an error (e), which is provided to the PIB. For example, the methanol concentration may be measured (e.g., in a recirculation path 139 between the fuel inlet to the anode chamber of the DMFC 103) and/or estimated from measurements from the DFMC system 100. The PIB integrates the error and combines the scaled integral term with the scaled error and the bias term ($\bar{u}$). The output of the PIB is limited to provide the control output ($u_{inj}$) for the pump speed for the methanol injection pump 121. The PIB output may be limited between, e.g., an upper limit $u_{max}$ and a lower limit $u_{min}$ of the injection pump speed.

Figure 4:
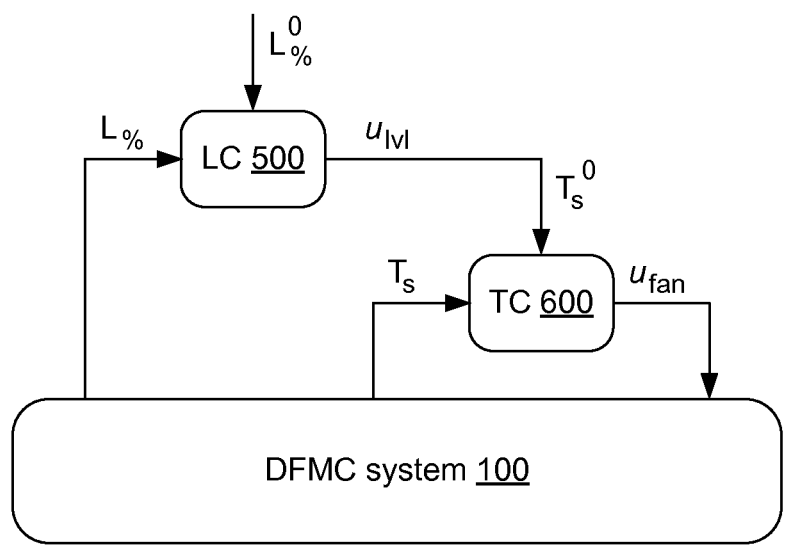
Figure 5:
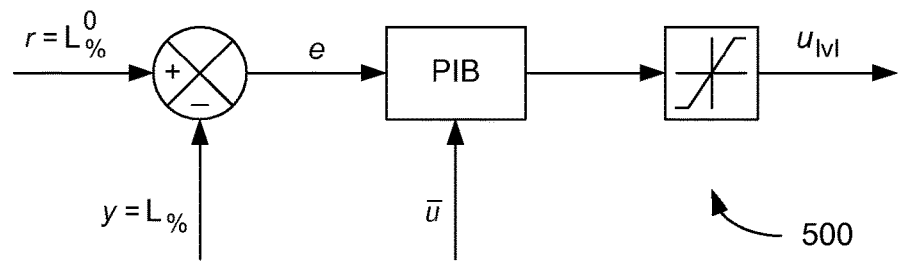
Figure 6:
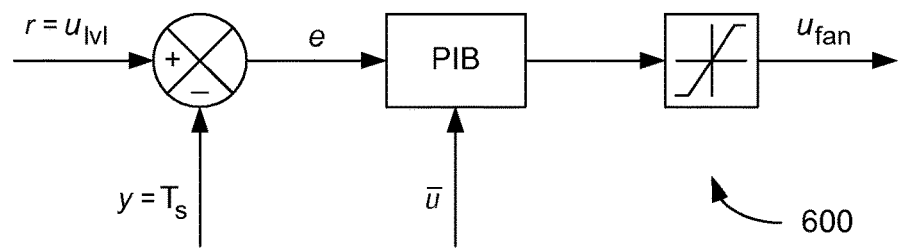

Referring next to FIG. 4 shown is a graphical representation of an example of cascading a liquid level controller 500 and a stack temperature controller 600 in accordance with various embodiment of the present disclosure. The liquid level controller 500 can act as the master and stack temperature controller 600 can act as the slave. In FIG. 4, the liquid level controller 500 receives an indication of the liquid level ($L_{\%}$ in percent) in the liquid tank 106 of the DFMC system 100 of FIG. 1. As illustrated in the example of FIG. 5, the liquid level $L_{\%}$ is compared to a reference setpoint ($L_{\%}^0$) to determine an error (e), which is provided to the PIB. The PIB integrates the error and combines the scaled integral term with the scaled error and the bias term ($\bar{u}$). The output of the PIB is limited to provide the control output ($u_{lvl}$). The PIB output may be limited between, e.g., an upper limit $u_{max}$ and a lower limit $u_{min}$ of the stack temperature of the DMFC 103 (FIG. 1). As shown in FIG. 4, $u_{max}$ is used as the stack temperature reference ($u_{lvl} = T_s^0$) of the stack temperature controller 600. The stack temperature controller 600 also receives an indication of the stack temperature ($T_s$) in the DFMC 103 of the DFMC system 100 of FIG. 1. As illustrated in the example of FIG. 6, the stack temperature $T_s$ is compared to the control output ($u_{lvl} = T_s^0$) of the liquid level controller 500 to determine an error (e), which is provided to the PIB. The PIB integrates the error and combines the scaled integral term with the scaled error and the bias term ($\bar{u}$). The output of the PIB is limited to provide the control output ($u_{fan}$) for the fan speed for the DFMC cooling fan 130. The PIB output may be limited between, e.g., an upper limit $u_{max}$ and a lower limit $u_{min}$ of the cooling fan speed.

An anti-reset windup technique may be used to maintain stable operation of the DMFC system 100. The anti-reset windup can include conditional integration that is based upon the indications of the measured (or estimated) variable y. That is, if the variable y is not within a determined range from $y_{min}$ to $y_{max}$, then the integration is suspended and the integral term does not change. This may be expressed as:

$$\text{if } y \notin [y_{min}, y_{max}] \Rightarrow I(t) = I(t - \Delta t),$$

where the minimum value $y_{min} = (y_1, y_2)$ and the maximum value $y_{max} = \max(y_1, y_2)$ are determined based upon:

$$y_1 = r + \frac{I(t - \Delta t) - (u_{max} - \bar{u})}{K_p} \text{ and}$$

-continued $$y_2 = r + \frac{I(t-\Delta t) - (u_{min} - \overline{u})}{K_p},$$

where each considers the bias term ($\overline{u}$) of the PIB.

In the case of the stack voltage controller 200 of FIG. 2, if the indicated stack voltage ($V_s$) for the current sampling point is outside the range based upon the integration term at the previous point (t−Δt), the upper and lower limits of the stack voltage, and the corresponding bias term, then the integral term I(t) for the current sampling point is the same as the integral term of the previous sampling point, i.e., I(t)=I(t−Δt). In the case of the methanol concentration controller 300 of FIG. 3, if the indicated methanol concentration ($C_{MeOH}$) for the current sampling point is outside the range based upon the integration term at the previous point (t−Δt), the upper and lower limits of the methanol concentration, and the corresponding bias term, then the integral term I(t) for the current sampling point is the same as the integral term of the previous sampling point, i.e., I(t)=I(t−Δt).

In the case of the cascaded liquid level controller 500 and the stack temperature controller 600 of FIG. 4, the anti-reset windup of the master controller is also tied to output of the slave controller. Thus, if the slave controller output saturates, then the integral term of the master controller is "frozen." This may be expressed as:

$$\text{if } y^{Master} \notin [y_{min}^{Master}, y_{max}^{Master}] \text{ or } u^{Slave} \notin [u_{min}^{Slave}, u_{max}^{Slave}] \Rightarrow I^{Master}(t) = I^{Master}(t-\Delta t).$$

Thus, in the case of the liquid level controller 500 of FIG. 5, if the indicated level of the liquid tank 106 (FIG. 1) for the current sampling point is outside the range based upon the integration term at the previous point (t−Δt), the upper and lower limits of the liquid level, and the corresponding bias term or if the control output ($u_{fan}$) of the stack temperature controller 600 is outside the upper and lower limits of the cooling fan speed, then the integral term I(t) for the current sampling point is the same as the integral term of the prevous sampling point, i.e., I(t)=I(t−Δt). The anti-reset windup of the slave controller is not affected by the master controller. In the case of the stack temperature controller 600 of FIG. 6, if the indicated stack temperature ($T_s$) for the current sampling point is outside the range based upon the integration term at the previous point (t−Δt), the upper and lower limits of the stack temperature, and the corresponding bias term, then the integral term I(t) for the current sampling point is the same as the integral term of the prevous sampling point, i.e., I(t)=I(t−Δt).

Control of the DMFC system 100 may be improved by selecting an appropriate sampling period for each of the controllers. The sampling periods may be based upon how quickly each of the measured or estimated variables y change over time. For example, the liquid level ($L_{\%}$) of the liquid tank 106 varies slower than the stack temperature ($T_s$) of the DMFC 103. Similarly, the stack voltage ($V_s$) for the DMFC 103 can vary faster than the other variables. By appropriately selecting the sampling period for each controller, variations in the operation of the DMFC system 100 can be reduced. For example, the sampling period of the liquid level ($L_{\%}$) for the liquid level controller 500 may be the longest at, e.g., one second. The sampling period of the stack temperature ($T_s$) for the stack temperature controller 600 may be shorter at, e.g., 0.5 second. The sampling period of the methanol concentration ($C_{MeOH}$) for the methanol concentration controller 300 may be shorter at, e.g., 0.5 second. The sampling period of the stack voltage ($V_s$) for the stack voltage controller 200 may be the shortest at, e.g., 0.25 second.

The stack current i(t) output by the DMFC 103 can be used as a feedback signal to the stack voltage controller 200. The stack current i(t) (or other monitored condition) may also be used as a feed forward signal to one of the PIB controllers. When using the stack current as a feed forward signal, the PIB control output u(t) may be expressed as:

$$u(t) = \overline{u} + K_p e(t) + K_I I(t) + K_F i(t),$$

where $K_F$ is the feed forward gain. For example, the stack current i(t) may be used as a feed forward signal by the methanol concentration controller 300, the liquid level controller 500, and/or the stack temperature controller 600. In some implementations, the scaled feed forward signal may be combined with the PIB control output (u(t)+$K_F$i(t)) to provide the corresponding control signal. In some embodiments, the output current of the DC/DC converter 136 may be used as a feed forward signal to one or more of the controllers.

One or more parameters of the PIB controllers and/or feed forward signals may be changed or updated during operation of the DMFC system 100. In this way, control of the DMFC system 100 may adapt to changing operating conditions. For example, changes in the ambient air temperature may be monitored and the system control may adapt to account for the effect on the DMFC operation. A parameter may be changed or updated by obtaining a new value from a lookup table, by calculating a new value using a predefined relationship (e.g., a mathematical expression), or other intelligent control method (e.g., neural networks and/or other rule based relationships). In some cases, an interface may be provided to allow a user to specify a parameter. Adaptive gain scheduling of one or more bias values ($\overline{u}$) may also be used to allow the PIB controllers to improve performance of the DMFC system 100. Changes or updates of the parameters may be carried out during the reactivation mode of the DMFC 103 to reduce the impact during the power production mode. In some cases, the reactivation mode may be initiated for the DMFC 103 in response to a monitored condition (e.g., ambient temperature) crossing a predefined threshold to allow one or more parameters to be updated.

Figure 7A:
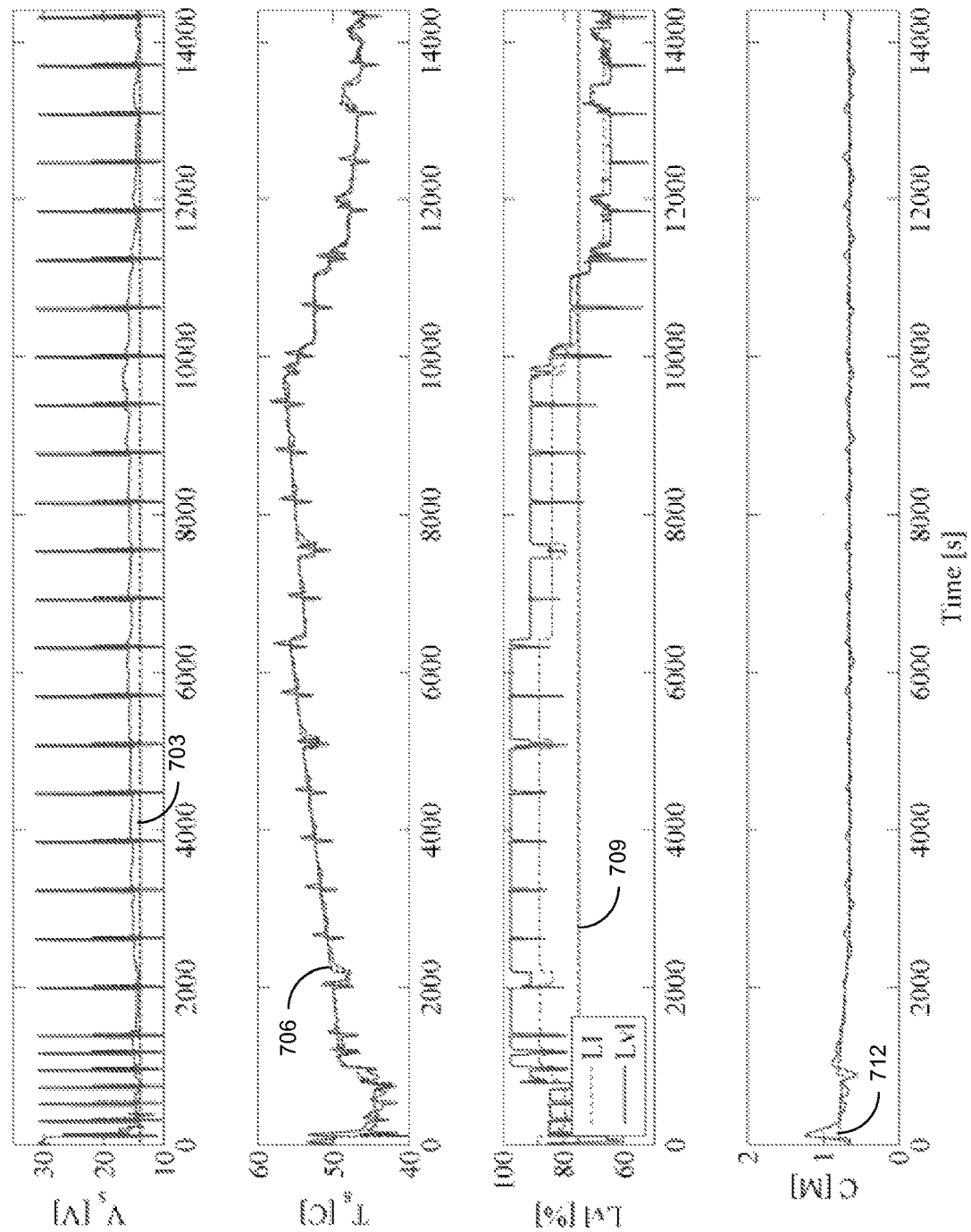
FIGS. 7A through 7E are plots illustrating the tested performance of a fuel cell system of FIG. 1 in accordance with various embodiments of the present disclosure.
Figure 7B:
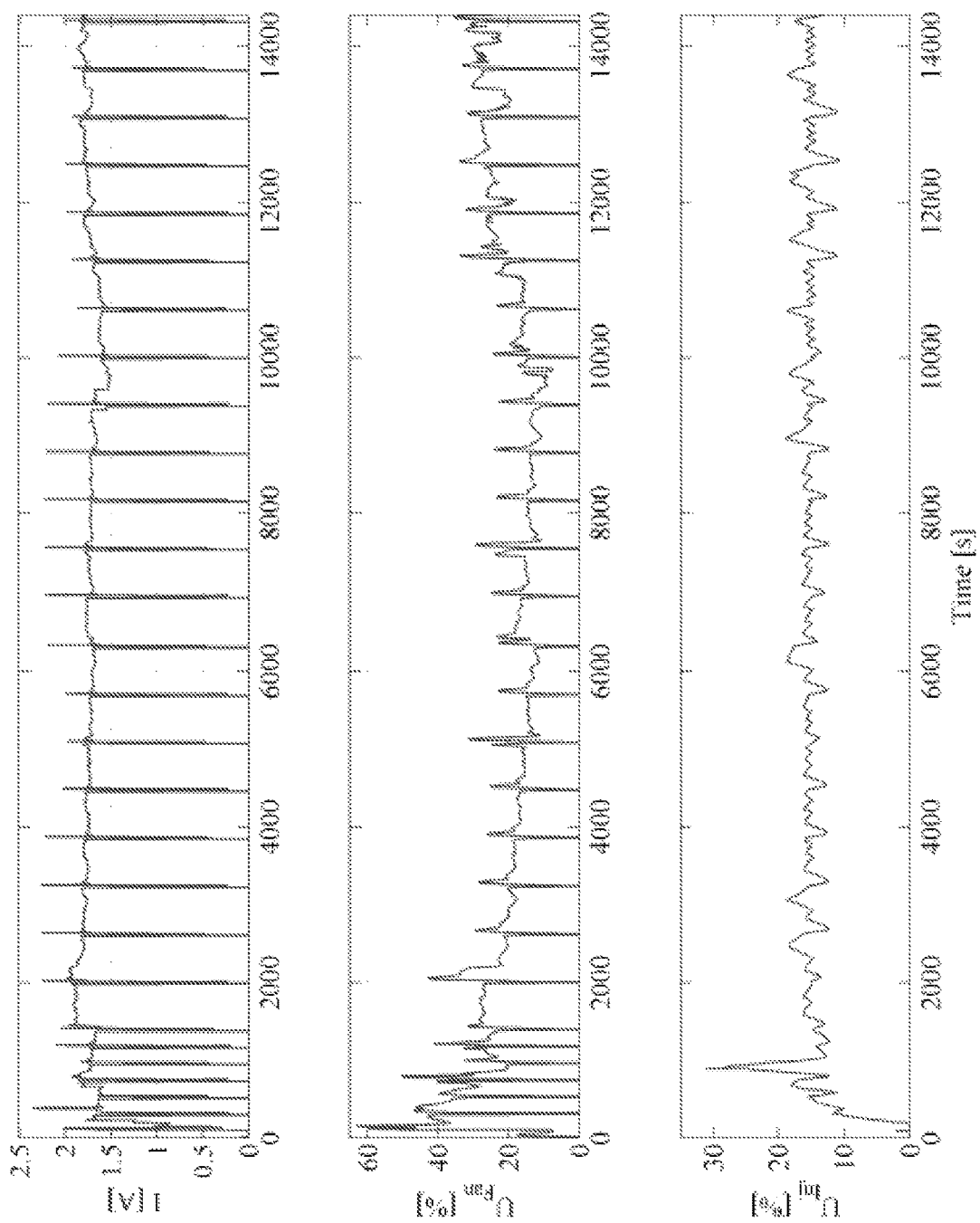
Figure 7C:
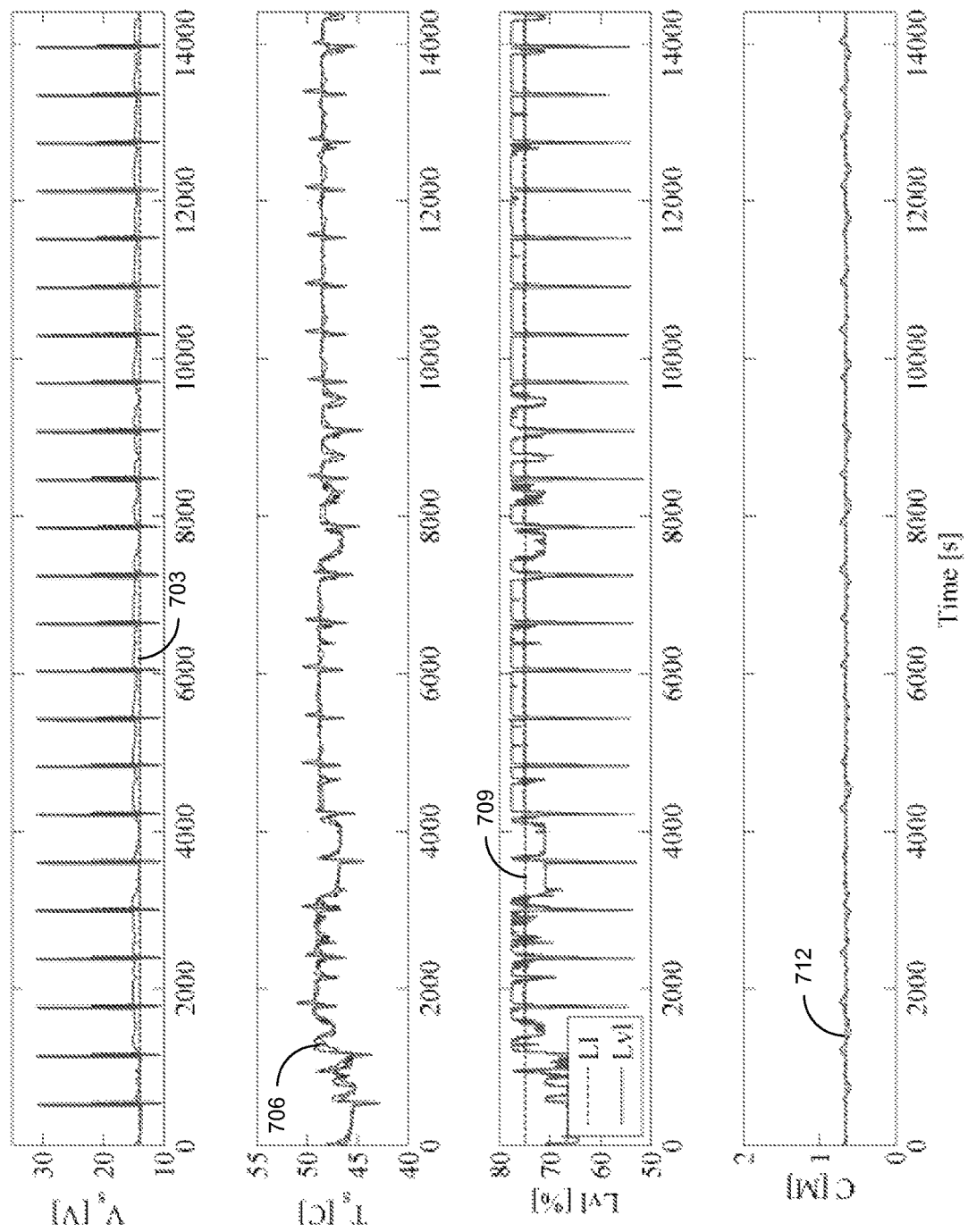
Figure 7D:
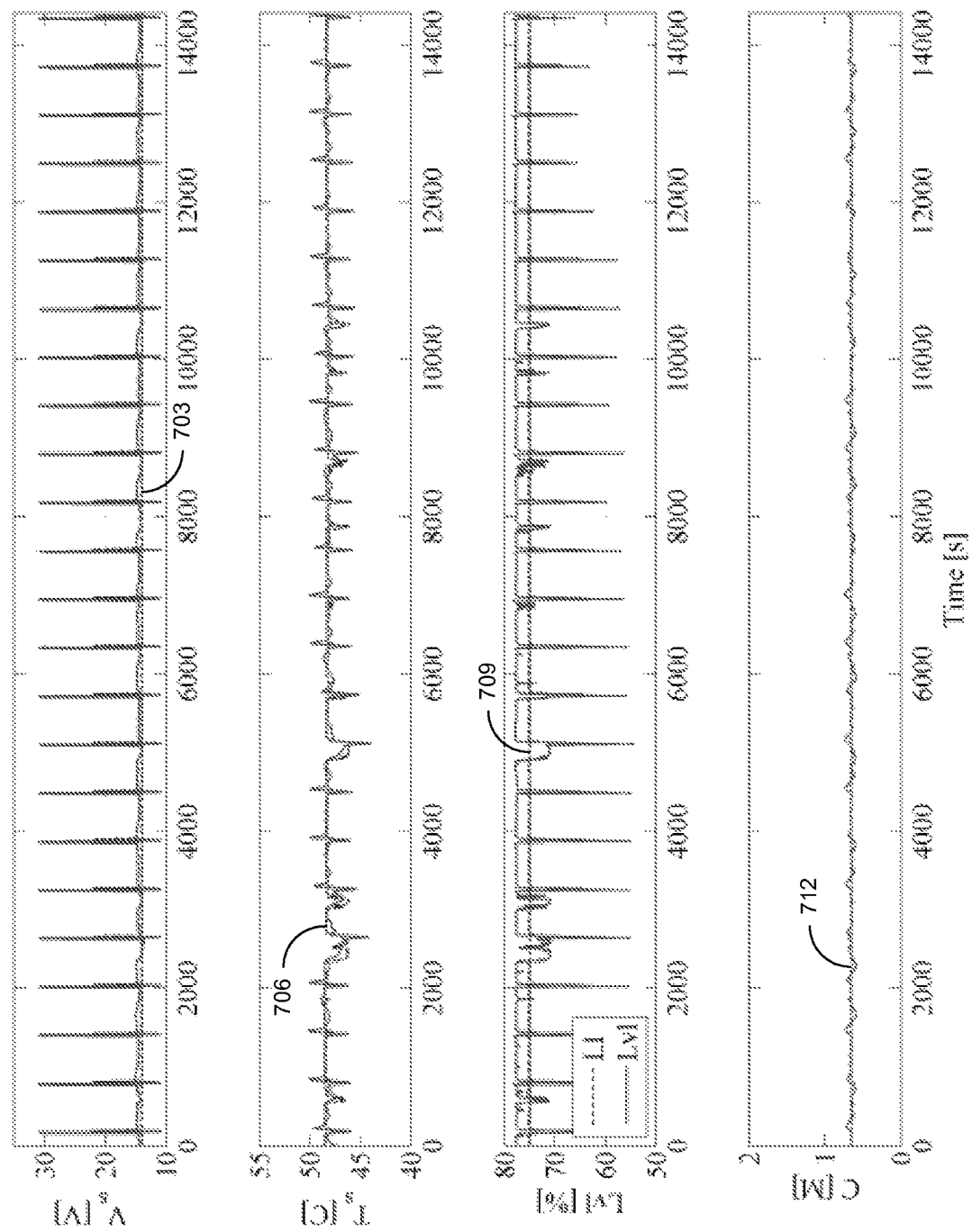
Figure 7E:
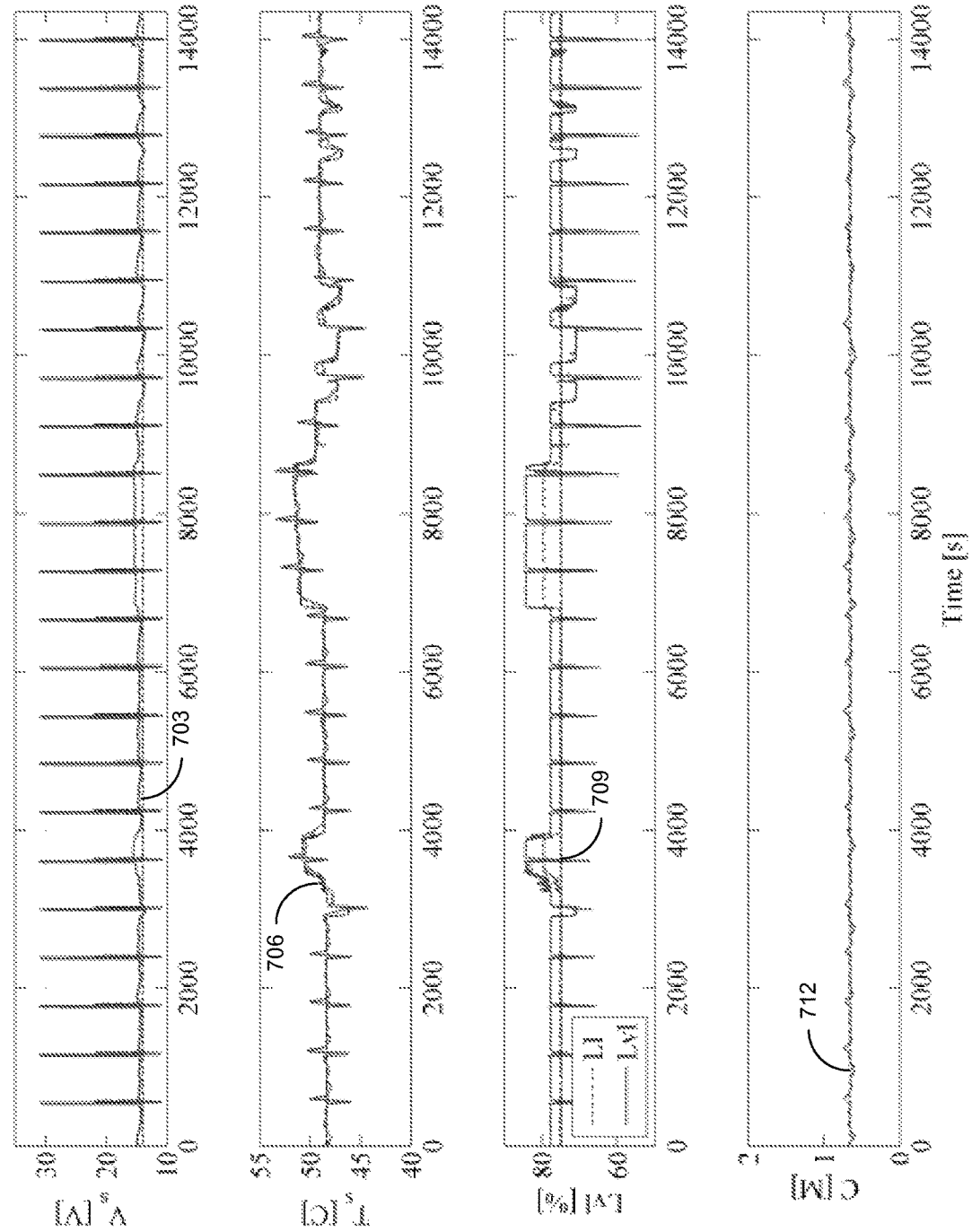

Testing of the DMFC system 100 with the disclosed controllers 200, 300, 500, and 600 (in the cascade configuration) extended the operating time of the DMFC system 100. It also provided significantly improved methanol concentration control (reduced deviation from the operating point) and temperature control (lower temperature rise for corresponding rise in tank level and reduced temperature fluctuations). Excellent water balance control was demonstrated by not triggering a water recovery mode with 16 hours of continuous operation. Referring to FIGS. 7A-7E, shown are examples of plots illustrating the tested performance of a DMFC system 100 over a 16-hour period. FIG. 7A depicts the stack voltage ($V_s$) in Volts, stack temperature ($T_a$) in ° C., the liquid level (Lvl) of the liquid tank 106 in %, and the methanol concentration (C) in M during the first 4-hour period. Dashed lines 703, 706, 709 and 712 indicate the set points for $V_s$, $T_s$, Lvl, and C, respectively. FIG. 7B provides stack current (I) in Amperes, the cooling fan speed ($U_{Fan}$), and the injection pump speed ($U_{Inj}$). FIGS. 7C, 7D and 7E depict $V_s$, $T_s$, Lvl, and C during the second, third and fourth 4-hour periods, respectively.

Control of the DMFC system 100 may also include estimating the methanol concentration of the fuel. An observer implemented by processing circuitry including, e.g., a processor executing instructions and/or code uses a plurality of monitored conditions and/or control variables to determine an estimate of the methanol concentration. For example, the estimated concentration may be based at least in part upon temperature of the anode chamber, cathode chamber, and/or stack membrane of the DMFC 103; temperature of the GLS 115; and/or level and/or temperature of the liquid tank 106. The estimated concentration may be based at least in part upon the control variables for the stack current ($u_{I_{DC}}$); the injection pump speed ($u_{inj}$); and/or the cooling fan speed ($u_{fan}$). The estimated methanol concentration may then be used as the methanol concentration ($C_{MeOH}$) input of the methanol concentration controller 300. A model of the DMFC time-evolving dynamics can be utilized for the estimation. The observer may be based upon linear or non-linear models of the system. A full-state observer or a reduced state observer may be used.

For a linear system, the dynamics may be modeled by:

$$\dot{x}(t) = Ax(t) + Bu(t)$$

$$y(t) = Cx(t) + Du(t)$$

where x(t) is the state vector, u(t) is the input vector of the system and y(t) is the output vector. The terms of the system matrices may be identified through input excitation and/or through the principles of mass/energy balance. An observer can be used to estimate the dynamics of the system using:

$$\dot{\hat{x}}(t) = A\hat{x}(t) + Bu(t) + L(y(t) - \hat{y}(t))$$

$$\hat{y}(t) = C\hat{x}(t) + Du(t)$$

where the estimated states are based upon the input and output vectors of the system. The term L is chosen such that as time approaches infinity, the error between the actual states and the estimated states ($\tilde{x}(t) = x(t) - \hat{x}(t)$) approaches zero or falls within a predefined limit. For stability, the eigenvalues of (A−LC) should be in the left half of the complex plane.

An observer in an augmented form (or an augmented observer) can also be used to estimate the dynamics of the system using:

$$\dot{\hat{x}} = A\hat{x} + Bu + L_p(y - \hat{y}) + L_a\hat{z}$$

$$\dot{\hat{z}} = L_i(y - \hat{y})$$

where the estimated states are again based upon the input and output vectors of the system where $L_p$ is the proportional gain, $L_a$ is the augmented-state gain, and $L_i$ is the integral gain. The equation for ŷ is the same as indicated above. The PI observer in the augmented form can be represented as:

$$\dot{\hat{\beta}} = \bar{A}\hat{\beta} + \bar{B}u + \bar{L}(y - \hat{y})$$

$$\hat{y} = \bar{C}\hat{\beta} + Du$$

where $$\hat{\beta} = \begin{bmatrix} \hat{x} \\ \hat{z} \end{bmatrix}$$

and $L = [L_p \ L_i]^T$.

The terms $L_p$, and $L_i$ are chosen such that as time approaches infinity, the error between the actual states and the estimated states ($\tilde{x}(t) = x(t) - \hat{x}(t)$) approaches zero or falls within a predefined limit. $L_a$ is chosen to enhance the performance of the estimator relative to the type of model disturbance. $L_a$ can be chosen to define within specified limits the space of observable disturbances for better estimation performance. This observer can also be used to enhance performance in the presence of process-model mismatch. For stability, the eigenvalues of (A−LC) should be in the left half of the complex plane.

For a non-linear system, the dynamics are linearized about an operating point ($\bar{x}, \bar{y}, \bar{u}$):

$$\begin{aligned} \dot{x}(t) &= f(x(t), u(t)) \\ y(t) &= g(x(t), u(t)) \end{aligned} \xrightarrow{\text{Linearize}} \begin{aligned} \Delta\dot{x}(t) &= A\Delta x(t) + B\Delta u(t) \\ \Delta y(t) &= C\Delta x(t) + D\Delta u(t) \end{aligned}$$

where $\Delta x = x - \bar{x}$, $\Delta y = y - \bar{y}$, and $\Delta u = u - \bar{u}$. The observer dynamics then become:

$$\Delta\dot{\hat{x}}(t) = A\Delta\hat{x}(t) + B\Delta u(t) + L(\Delta y(t) - \Delta\hat{y}(t))$$

$$\Delta\hat{y}(t) = C\Delta\hat{x}(t) + D\Delta u(t)$$

The term L is chosen such that as time approaches infinity, the error between the actual states and the estimated states ($\Delta\tilde{x}(t) = \Delta x(t) - \Delta\hat{x}(t)$) approaches zero. The dynamics of the augmented observer can be linearized in the same fashion as can be appreciated.

In the case of the non-linear DMFC system 100 (FIG. 1), the state vector x(t) may include the anode chamber temperature ($T^{ACH}$), the temperature of the gas liquid separator 115 ($T^{GLS}$), the liquid level of the liquid tank 106 ($L^{TANK}$), the temperature of the liquid tank 106 ($T^{TANK}$), the stack membrane temperature ($T^{SM}$), the cathode chamber temperature ($T^{CCH}$), and the methanol concentration ($C_{CH_3OH}$). The output vector y(t) may include $T^{ACH}$, $T^{GLS}$, $L^{TANK}$, and $T^{TANK}$. The output vector may also include $T^{SM}$ and/or $T^{CCH}$. The output vector may also include other variable such as, e.g., temperature, relative humidity and/or pressure of the air supplied to and/or exiting the cathode chamber of the DMFC 103. The input vector u(t) can include the stack current ($I^{STACK}$), the speed of the injection pump 121 (InjSpeed), and the speed of the cooling fan 130 (FanSpeed). During testing, a set of system equations was determined and tested using Simulink. The linear and non-linear state observers were examined during the simulation tests, which determined that both the linear and non-linear observers provided good estimation results for the methanol concentration in the fuel. In one example, the eigenvalues of A were determined to be λ(A)=[−487.91 −11.4 −0.2 −0.04 −0.009 −0.003 −0.00] and the eigenvalues of (A−LC) were chosen for a pole placement to stabilize the loop such that:

$$\lambda(A-LC) = [-500 \ -50 \ -1 \ -0.5 \ -0.3 \ -0.1 \ -0.05]$$

The calculated values of L were given by:

$$L = \begin{bmatrix} 51.33 & -0.31 & 0.39 & -2.25 \\ -0.05 & 0.14 & 0.11 & 0.02 \\ 0.45 & 0.11 & 0.37 & 0.11 \\ -2.48 & 0.07 & 0.11 & 0.53 \\ -613 & -0.42 & 0.57 & -2.89 \\ 168.31 & 1126.3 & -162.5 & 8136.5 \\ 1.53 & -0.05 & 0.06 & -0.26 \end{bmatrix}$$

Figure 8A:
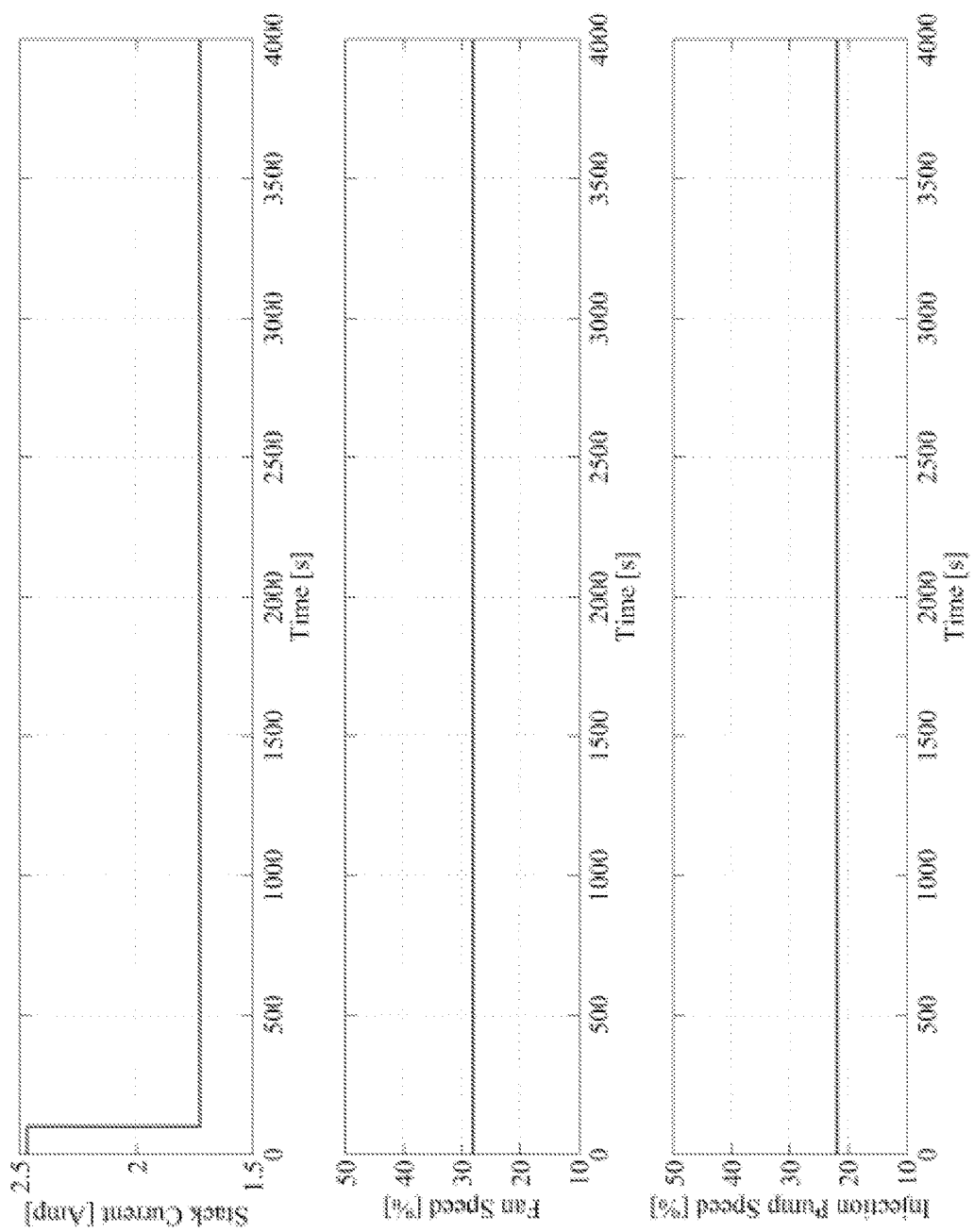
FIGS. 8A and 8B are plots illustrating methanol concentration estimation simulation results for full state observers in accordance with various embodiments of the present disclosure.
Figure 8B:
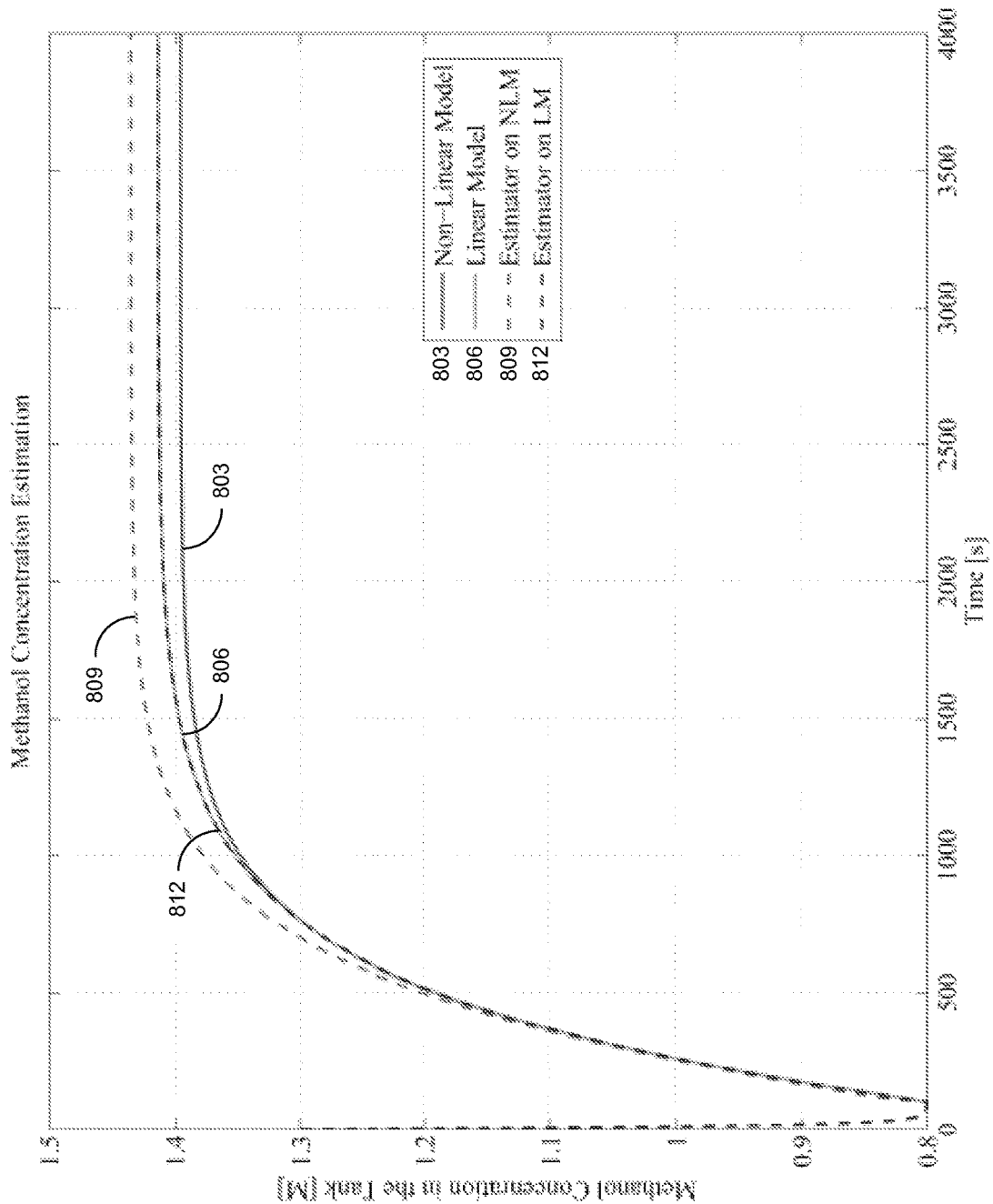

Referring to FIGS. 8A and 8B, shown is an example of methanol concentration estimation simulation results for the full state observers. FIG. 8A illustrates the input signals and FIG. 8B shows the methanol concentrations for the non-linear and linear models (curves 803 and 806, respectively) and the estimator outputs for the non-linear and linear cases (curves 809 and 812, respectively). Performance of the observer for a methanol concentration range of 0.8±0.5 M is shown in the following table.

| Inputs | Step Changes | Steady State Observer Error |
|---|---|---|
| Stack Current | +23 & −25% of OP | 0.07 & 0.03M |
| Fan Speed | −50 & +50% of OP | 0.05 & 0.04M |
| Injection Pump Speed | −18 & +25% of OP | 0.097 & 0.12M |

Figure 9A:
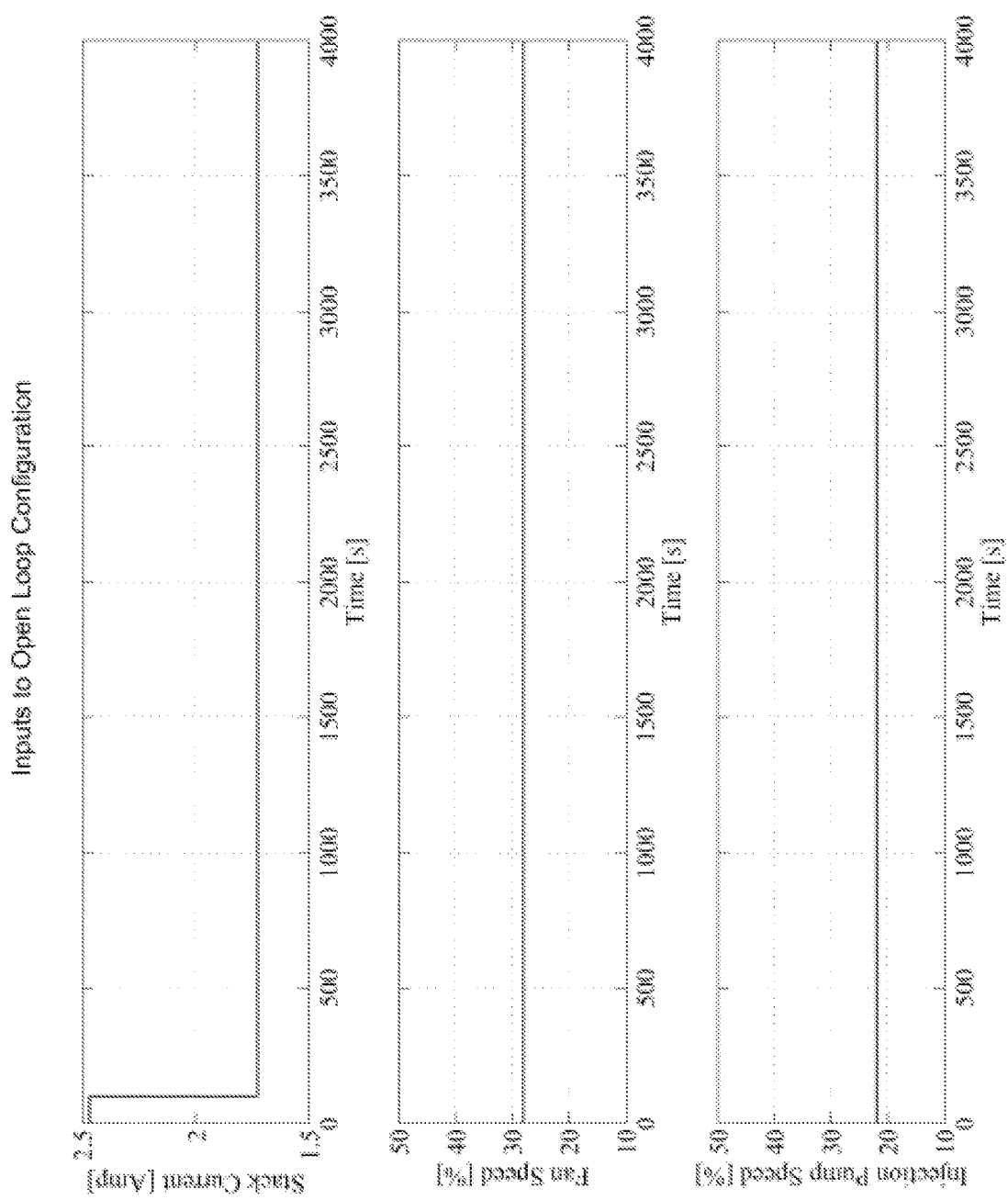
FIGS. 9A and 9B are plots illustrating methanol concentration estimation simulation results for reduced state observers in accordance with various embodiments of the present disclosure.
Figure 9B:
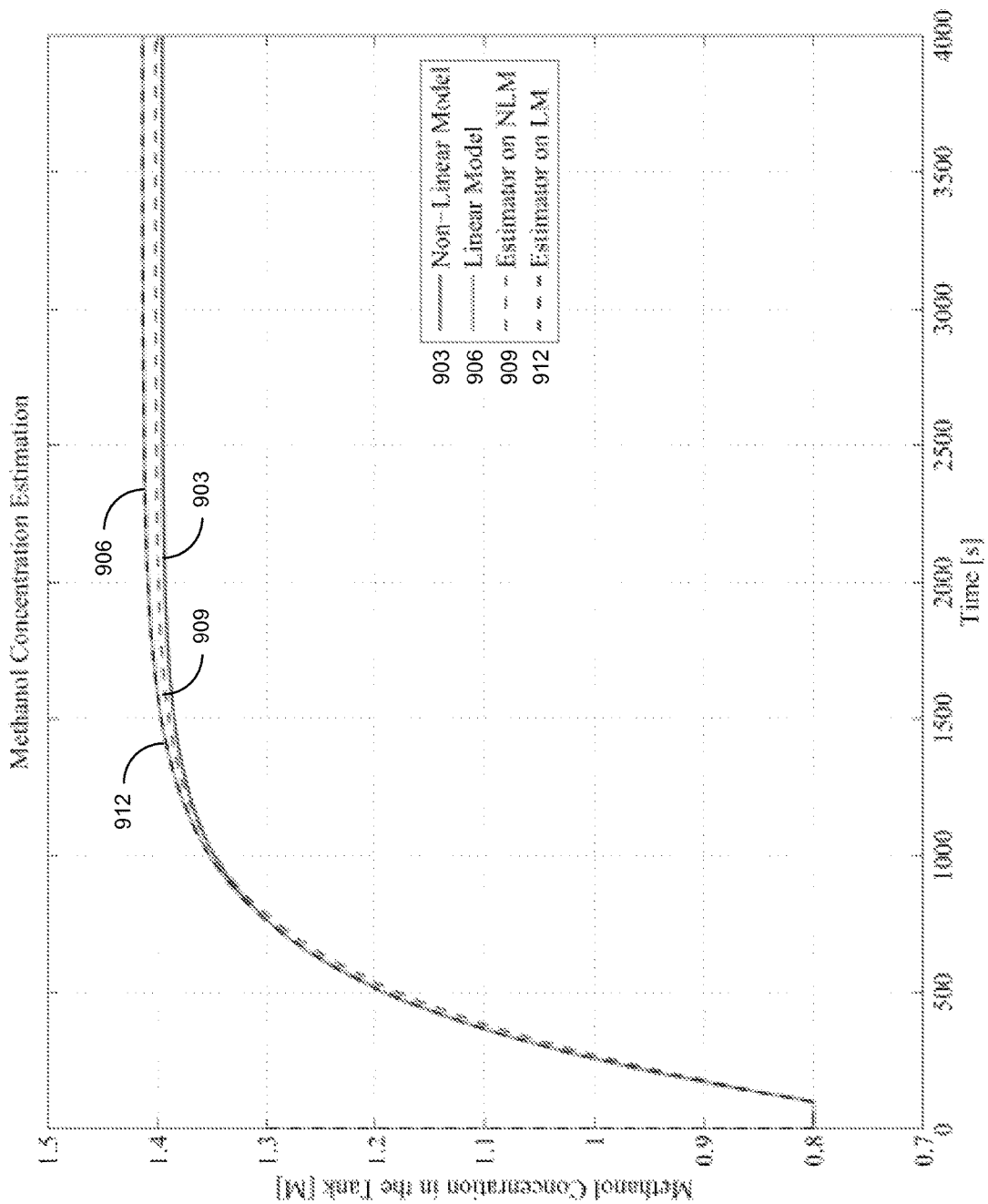

Because some of the state vector terms can be measured, a reduced state observer can be used to reduce the computation to estimate methanol concentration. This may be expressed as:

$$\begin{bmatrix} \dot{x}_1 \\ \dot{x}_2 \end{bmatrix} = \begin{bmatrix} A_{11} & A_{12} \\ A_{21} & A_{22} \end{bmatrix}\begin{bmatrix} x_1 \\ x_2 \end{bmatrix} + \begin{bmatrix} B_1 \\ B_2 \end{bmatrix}u$$

$$y = \begin{bmatrix} I_k & 0 \\ C_{21} & C_{22} \end{bmatrix}\begin{bmatrix} x_1 \\ x_2 \end{bmatrix}$$

where only $x_2$ is estimated instead of the entire state vector $x(t)$. In some implementations, $x_2$ may estimate a plurality of terms that may not be measured directly. In other embodiments, the methanol concentration may be the only estimated term. Using the measured state vector terms, simulation tests of the reduced state observer resulted in faster convergence than for the full state estimation tests and with lower steady state observer errors. Referring to FIGS. 9A and 9B, shown is an example of methanol concentration estimation simulation results for the reduced state observers. The chosen eigenvalues were:

$$\lambda(A_{22} - LA_{12}) = \begin{bmatrix} -3 \\ -2 \\ -1 \end{bmatrix}$$

and the calculated L was:

$$L = \begin{bmatrix} -55.55 & 0 & -0.006 & -1.85 \\ -0.05 & 0 & -8.89 & 626.41 \\ -0.004 & 0 & -0.12 & 19.64 \end{bmatrix}$$

FIG. 9A illustrates the input signals and FIG. 9B shows the methanol concentrations for the non-linear and linear models (curves 903 and 906, respectively) and the estimator outputs for the non-linear and linear cases (curves 909 and 912, respectively). Performance of the observer for a methanol concentration range of 0.8±0.5 M is shown in the following table.

| Inputs | Step Changes | Steady State Observer Error |
|---|---|---|
| Stack Current | +23 & −25% of OP | 0.02-0.004M |
| Fan Speed | −50 & +50% of OP | 0.008-0.004M |
| Injection Pump Speed | −18 & +25% of OP | 0.04-0.09M |

The reduced state observer performed better than the full state observer with a maximum error of 0.09 M. In some embodiments, other combinations of states of the DMFC system 100 may be used to estimate the methanol concentration.

Figure 10:
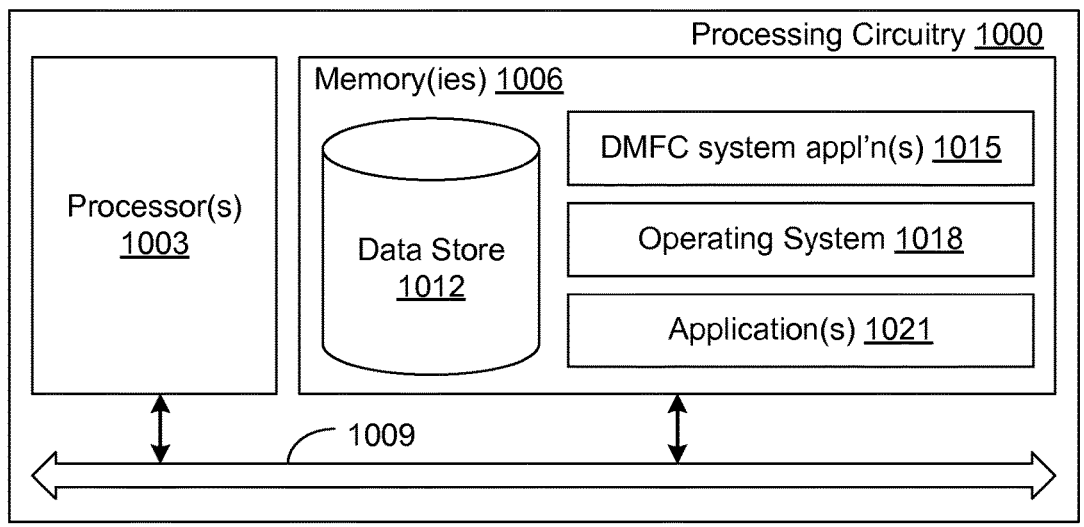
FIG. 10 is a schematic block diagram that illustrates an example of processing circuitry employed in the fuel cell system of FIG. 1 in accordance with various embodiments of the present disclosure.

With reference now to FIG. 10, shown is a schematic block diagram of an example of processing circuitry 1000 that may be used to implement various portions of the control of the DMFC system 100 of FIG. 1 in accordance with various embodiments of the present disclosure. The processing circuitry 1000 includes at least one processor circuit, for example, having a processor 1003 and a memory 1006, both of which are coupled to a local interface 1009. To this end, the processing circuitry 1000 may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. The local interface 1009 may comprise, for example, a data bus with an accompanying address/control bus or other bus structure as can be appreciated. The processing circuitry 1000 can include a display for rendering of generated graphics such as, e.g., a user interface and an input interface such as, e.g., a keypad or touch screen to allow for user input. In addition, the processing circuitry 1000 can include communication interfaces (not shown) that allow the processing circuitry 1000 to communicatively couple with other communication devices. The communication interfaces may include one or more wireless connection(s) such as, e.g., Bluetooth or other radio frequency (RF) connection and/or one or more wired connection(s).

Stored in the memory 1006 are both data and several components that are executable by the processor 1003. In particular, stored in the memory 1006 and executable by the processor 1003 are DMFC system application(s) 1015, an operating system 1018, and/or other applications 1021. DMFC system applications can include applications that support, e.g., controllers for control of the operation of the DMFC system 100 and/or reduced observers for estimation of states of the DMFC system 100. It is understood that there may be other applications that are stored in the memory 1006 and are executable by the processor 1003 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, LabVIEW® or other programming languages.

A number of software components are stored in the memory 1006 and are executable by the processor 1003. In this respect, the term "executable" means a program file that is in a form that can ultimately be run by the processor 1003. Examples of executable programs may be, for example, a compiled program that can be translated into machine code in a format that can be loaded into a random access portion of the memory 1006 and run by the processor 1003, source code that may be expressed in proper format such as object code that is capable of being loaded into a random access portion of the memory 1006 and executed by the processor 1003, or source code that may be interpreted by another executable program to generate instructions in a random access portion of the memory 1006 to be executed by the processor 1003, etc. An executable program may be stored in any portion or component of the memory 1006 including, for example, random access memory (RAM), read-only memory (ROM), hard drive, solid-state drive, USB flash drive, memory card, optical disc such as compact disc (CD)

or digital versatile disc (DVD), floppy disk, magnetic tape, or other memory components.

The memory 1006 is defined herein as including both volatile and nonvolatile memory and data storage components. Volatile components are those that do not retain data values upon loss of power. Nonvolatile components are those that retain data upon a loss of power. Thus, the memory 1006 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1003 may represent multiple processors 1003 and the memory 1006 may represent multiple memories 1006 that operate in parallel processing circuits, respectively. In such a case, the local interface 1009 may be an appropriate network that facilitates communication between any two of the multiple processors 1003, between any processor 1003 and any of the memories 1006, or between any two of the memories 1006, etc. The local interface 1009 may comprise additional systems designed to coordinate this communication, including, for example, performing load balancing. The processor 1003 may be of electrical or of some other available construction.

Although the DMFC system application(s) 1015, the operating system 1018, application(s) 1021, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including the DMFC system application(s) 1015 and/or application(s) 1021, that comprises software or code can be embodied in any non-transitory computer-readable medium for use by or in connection with an instruction execution system such as, for example, a processor 1003 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A system for operational control of a fuel cell, comprising:
    the fuel cell comprising an anode chamber operable to receive fuel from a liquid fuel tank and a cathode chamber operable to receive ambient air;
    a liquid level controller operable to provide a control output based at least in part upon an indication of a liquid level of the liquid fuel tank and a level reference; and
    a stack temperature controller in cascade with the liquid level controller, the stack temperature controller operable to provide a fan speed control output based at least in part upon an indication of a stack temperature of the fuel cell and the control output of the liquid level controller, where the ambient air received by the cathode chamber is based at least in part upon the fan speed control output.

2. The system of claim 1, wherein the fuel cell is a direct methanol fuel cell.

3. The system of claim 1, wherein the liquid level controller and the stack temperature controller are proportional-integral-bias (PIB) controllers.

4. The system of claim 1, wherein the liquid level controller and the stack temperature controller comprise anti-reset windup that limits an integral term of the liquid level and stack temperature controllers.

5. The system of claim 4, wherein the anti-reset windup of the liquid level controller is based upon the liquid level of the liquid fuel tank and the fan speed control output of the stack temperature controller.

6. The system of claim 5, wherein the anti-reset windup of the liquid level controller is initiated when the liquid level falls outside of a corresponding operating range or the fan speed control output falls outside of a corresponding operating range.

7. The system of claim 6, wherein the operating range corresponding to the liquid level is based at least in part upon a bias corresponding to the liquid level controller.

8. The system of claim 4, wherein the anti-reset windup of the stack temperature controller is based upon the stack temperature of the fuel cell.

9. The system of claim 4, wherein the anti-reset windup of the stack temperature controller is initiated when the stack temperature falls outside of a corresponding operating range that is based at least in part upon a bias corresponding to the stack temperature controller.

10. The system of claim 1, comprising a methanol concentration controller operable to provide an injection pump control output based at least in part upon an indication of a methanol concentration of the fuel.

11. The system of claim 10, wherein the methanol concentration controller is a proportional-integral-bias (PIB) controller.

12. The system of claim 10, wherein the methanol concentration controller comprises an anti-reset windup that limits an integral term of the methanol concentration controller based upon the methanol concentration of the fuel.

13. The system of claim 12, wherein the anti-reset windup of the methanol concentration controller is initiated when the methanol concentration falls outside of a corresponding operating range that is based at least in part upon a bias corresponding to the methanol concentration controller.

14. The system of claim 10, wherein the indication of the methanol concentration is an estimate of the methanol concentration generated by a reduced state observer.

15. The system of claim 14, wherein the reduced state observer is based upon an observer in an augmented form.

16. The system of claim 1, comprising a stack voltage controller operable to provide a stack current control output based at least in part upon an indication of a stack voltage of the fuel cell.

17. The system of claim 16, wherein the stack voltage controller is a proportional-integral-bias (PIB) controller.

18. The system of claim 16, wherein the stack voltage controller comprises an anti-reset windup that limits an integral term of the stack voltage controller based upon the stack voltage of the fuel cell.

* * * * *